United States Patent [19]

Hirohara et al.

[11] 4,239,854

[45] Dec. 16, 1980

[54] ENZYME-IMMOBILIZATION CARRIERS AND PREPARATION THEREOF

[75] Inventors: Hideo Hirohara; Shigeyasu Nabeshima, both of Ibaraki; Tsuneyuki Nagase, Takatsuki, all of Japan

[73] Assignee: Sumitomo Chemical Company, Limited, Osaka, Japan

[21] Appl. No.: 899,466

[22] Filed: Apr. 24, 1978

[51] Int. Cl.³ .............................. C09J 8/00; C08G 2/00
[52] U.S. Cl. ......................................... 521/31; 521/35
[58] Field of Search ....................... 521/31, 38, 39, 25, 521/35

[56] References Cited

U.S. PATENT DOCUMENTS

| | | | |
|---|---|---|---|
| 2,575,518 | 11/1951 | Holmes | 210/24 |
| 3,663,467 | 5/1972 | Albright | 521/30 |
| 3,991,018 | 11/1976 | Strok et al. | 521/31 |
| 4,097,420 | 6/1978 | Mikes et al. | 521/31 |
| 4,146,432 | 3/1979 | Hirohara et al. | 195/63 |

FOREIGN PATENT DOCUMENTS 598130  7/1946  United Kingdom ...................... 521/35

OTHER PUBLICATIONS

Journal of Agricultural Food Chem., vol. 21, No. 3, 1973-Olson, et al.
Biotech. & Bioeng. 15, 597–602, (1973), Stanby, et al.
J. Amer. Chem. for 84 305–306 (1962).
Polymer Letters vol. 2, 587–591 (1964).
Advances on Polymertriene 5, 172–173 (1967).
J. Amer. Chem. for 81, 4024–4028 (1959).

*Primary Examiner*—Joseph L. Schofer
*Assistant Examiner*—Peter F. Kulkosky
*Attorney, Agent, or Firm*—Cushman, Darby & Cushman

[57] ABSTRACT

Enzyme-immobilization carriers which comprise a macroporous amphoteric ion-exchange resin having a cation-exchange capacity due to carboxymethyl groups of 0.5 meq/g-dry resin or more, an anion-exchange capacity of 1 meq/g-dry resin or more, and a specific surface area of 1 m²/g-dry resin or more, the total volume of macropores having a diameter of 100 Å to 2000 Å being 0.1 cc/g-dry resin or more, and a process for producing said carriers.

12 Claims, No Drawings

ENZYME-IMMOBILIZATION CARRIERS AND PREPARATION THEREOF

The present invention relates to carriers for immobilizing enzyme thereto (referred to as "enzyme-immobilization carriers" hereinafter) and preparation thereof. More particularly, it relates to enzyme-immobilization carriers which comprise a macroporous synthetic polymer having both anion-exchange groups of 1 meq/g-dry resin or more and carboxymethyl groups of 0.5 meq/g-dry resin or more (in the present invention, all the terms "resin" mean synthetic resin other than polysaccharides and derivatives thereof) and to preparation thereof.

On account of the usefulness of immobilized enzymes in industrial uses, a number of techniques for enzyme-immobilization have recently been developed [C. R. Zaborsky: Immobilized Enzymes (published from C.R.C. Press, 1973)]. Therefore, a large number of enzyme-immobilization carriers are well known. Of these carriers, polysaccharides and their derivatives, for example, celluloses, crosslinked dextrans and ionic derivatives thereof, are widely used and some of them gain a fair success. But the polysaccharides have many drawbacks as follows: Mechanical strengths are poor; in column operation, a sufficient flow rate is difficulty obtained and blocking is easy to occur; and polysaccharides are easily attacked by microorganisms. Further, when enzymes are immobilized to ionic polysaccharide derivatives through an ionic linkage, they are easily released therefrom by reaction solutions or product solutions having a little high concentration of electrolyte. This is a serious problem in practical use.

On the other hand, using ion-exchange resins as an enzyme-immobilization carrier was already known in the latter half of 1950 [J. Amer. Chem. Soc., Vol. 81, 5133-5136 (1959)]. But, the amount of enzyme immobilized per unit weight of carrier is very small and the activity of resulting immobilized enzymes is very low so that practical value was regarded as very low. Ion-exchange resins made of synthetic resins as matrix are however more superior to polysaccharides and derivatives thereof in many points described below: Mechanical strengths are high; the resins withstand long-term operation in large columns with a relatively low degree of damage; sufficient flow rate can be ensured in column operation on account of a suitable particle size; resistance to attack of microorganisms is high; and cost is low.

The inventors extensively studied to develop carriers, by making use of the advantages of ion-exchange resins, which provide immobilized enzymes having high activity and long life time as catalysts, and moreover which enable enzymes to be immobilized thereto in large amounts. As a result, it was found that the so-called macroporous resins or macroreticular resins which are made of amphoteric ion-exchange resins having both carboxymethyl (referred to as "CM" hereinafter) groups having unique affinity to many enzyme proteins and anion-exchange groups such as a primary, secondary or tertiary amino group or quaternary ammonium group, and besides which have a large number of macropores of about 100 Å to several thousand Å in diameter and therefore have large specific surface area and pore volume, are a superior carrier satisfying the aforesaid requirements. Particularly, said macroporous or macroreticular resins proved to be a superior carrier in practical use since they provide immobilized enzymes which are very long in life time (stability in operation) regarded as particularly an important factor in a long-term continuous operation with immobilized enzymes. The inventors thus attained to the present invention.

An object of the present invention is to provide enzyme-immobilization carriers which provide immobilized enzymes having both high activity and long life time (stability), and besides which enable enzymes to be immobilized in large amounts per unit weight of carrier, and preparation thereof.

Another object of the present invention is to provide enzyme-immobilization carriers suitable for industrial use which immobilize enzymes which are in themselves a catalyst for reaction in homogeneous aqueous media, thereby enhancing the stability of the enzymes and making them suitable for repeated or continuous use, and preparation thereof.

The reasons why amphoteric ion-exchange resins having both CM groups and anion-exchange groups (e.g. amino group) are superior as carriers for enzyme-immobilization and provide immobilized enzymes having long life time (stability), may be considered as follows: Because of the similarity of the ion-exchange groups in carrier to the ionic groups (i.e. carboxyl groups and amino groups) in enzyme molecules, affinity between carrier and enzyme probably becomes large.

The amphoteric ion-exchange resins of the present invention are produced by various methods, but a simple and desirable method is introduction of CM groups into macroporous anion-exchange resins. The introduction of CM groups is achieved by reacting a compound of the formula,

$$XCH_2COOY$$

wherein Y is a halogen atom and Y is a hydrogen atom or an alkali metal, with a macroporous synthetic resin having a hydroxyl, primary amino, secondary amino, imino or sulfhydryl group, or derivative thereof in the presence of an alkaline compound. In order to obtain highly CM-substituted resins, it is essential to wet the resin with the reaction solution far in the inner parts of the macropores. When the CM-substitution is insufficient at one reaction, it is well achieved by repeating the reaction twice, three times and so on. Of the CM-reagents, monochloroacetic acid and its sodium salt are most favorable in terms of reactivity and economy. The amount of CM-reagent used depends upon the degree of CM-substitution of the resins, but less CM-substituted resins are not important in view of the spirit of the present invention. For allowing the reaction to proceed rapidly, it is generally favorable to use CM-reagents in excess of stoichiometric amount. It is very difficult to know exact mole numbers of the resin to be CM-substituted. A preferred amount of CM-reagent empirically obtained is about ½ to about 10 parts, preferably ⅔ to 3 parts, based on 1 part of dry resin. In the present invention, the dry weight of resin is measured as follows: Anion-exchange resins and amphoteric ion-exchange resins are converted to the OH-form and H-form, respectively, and neutral resins having no ion-exchange groups are washed progressively with an acid, alkali and then a large amount of water; after conditioning, the resins are vacuum-dried at 60° C. for more than 6 hours and allowed to stand constant weight at room temperature of 18° to 25° C. for more than 2 hours; and then the resins are weighed. In the description given hereinafter, the weights of resin and carrier always mean a dry weight obtained by the above method, if not particularly referred to.

As the alkaline compound, alkali metal hydroxides (e.g. sodium hydroxide, potassium hydroxide), alkaline earth metal hydroxides (e.g. magnesium hydroxide, calcium hydroxide) and in some cases organic amines (e.g. triethylamine) are used. Among those, sodium hydroxide is most preferred. The amount of alkaline compound used is preferably about ⅓ to about 2 times by mole based on the CM-reagent. In the CM-substitution, a side reaction producing glycolic acid proceeds. When the amount of alkaline compound is too large, the side reaction increases and the efficiency of CM-reagent becomes poor. Accordingly, the most preferred amount of alkaline compound is about ⅓ to about 2 times by mole based on the CM-reagent.

As the resins to be CM-substituted, the macroporous resins as described below meet the spirit of the present invention that the resins are a carrier for immobilized enzymes having excellent practical performances as industrial catalysts. That is the macroporous resins are such that they have one or more functional groups selected from the group consisting of hydroxyl, primary amino, secondary amino, imino and sulfhydryl groups, have a large number of macropores of about 100 Å to several thousand Å in diameter in addition to micropores produced depending upon the degree of crosslinking and therefore have large pore volumes and large specific surface areas.

The macropores are physically produced by special polymerization method and are suitable for continuous operation since they have physical strengths superior to gel type resins having micropores only. The macroporous resins are also called a MR type resin, MP type resin, macroreticular type resin or highly porous type resin. In order that the macroporous resins may clearly display an enzyme-immobilizing effect, it is necessary that the specific surface area of the resins is at least 1 $m^2$/g-resin, more preferably 5 $m^2$/g-resin or more, and besides that the total pore volume of the macropores having a diameter of 100 Å to 2000 Å is at least 0.1 cc/g-resin, more preferably 0.2 cc/g-resin. The specific surface area is obtaied by measuring the surface area of dry resin according to the nitrogen adsorption method using the surface area measuring instrument of Carlo-Erbo Co. and calculating according to the BET method. The pore diameter and pore volume are obtained by measurement on the Hg-penetration porosimeter of Carlo-Erbo Co. and calculation on the assumption that the macropores are of a cylindrical form having a circular crosssection. Pores having a diameter of more than 2000 Å do not contribute to the stabilization of immobilized enzymes since they have much larger dimensions than the enzymes. A preferred mean pore diameter depends upon the kind of enzyme to be immobilized, but generally it is often within the range of 150 Å to 1000 Å.

Macroporous resins meeting the above-described requirements can be produced by the well-known processes, but ready-made articles (mainly made of anion-exchange resins) are on the market and easily available. Many of such articles mainly have a hydroxyl, aliphatic primary amino or aliphatic secondary amino group, and those having a sulfhydryl, imino or aromatic imino group are very few. Some examples of the articles and their physical and chemical properties are shown in the following table.

| Trade Name | Manufacturing company | Matrix | Feature of ion-exchange group | Functional group capable of CM-substitution | Specific surface area ($m^2$/g-resin) | Total pore* volume (cc/g-resin) | Mean pore diameter (Å) | Ion-exchange capacity (meq/g-resin) |
|---|---|---|---|---|---|---|---|---|
| Duolite A-4 | Diamond Shamrock Co. | phenolic | Tertiarized polyethylene polyamine | —OH | 68.1 | 0.563 | 250 | 4.38 |
| Duolite A-6 | Diamond Shamrock Co. | phenolic | Tertiarized polyethylene polyamine | —OH | 24.6 | 0.600 | 400 | 5.31 |
| Duolite A-7 | Diamond Shamrock Co. | phenolic | Polyethylene polyamine | —OH, —$NH_2$, —NHR | 31.6 | 0.534 | 420 | 7.10 |
| Duolite S-30 | Diamond Shamrock Co. | phenolic | — | —OH | 90.3 | 0.605 | 340 | 0 |
| Duolite S-37 | Diamond Shamrock Co. | phenolic | Partially tertiarized polyethylene polyamine | —OH, —NHR | 95.3 | 0.680 | 290 | 4.24 |
| Amberlite IR-45 | Rohm & Haas Co. | polystyrene | Polyethylene polyamine | —$NH_2$, —NHR | 2.2 | 0.128 | 1460 | 3.90 |
| Diaion WA-20 | Mitsubishi Kasei Co. | polystyrene | Polyethylene polyamine | " | 4.6 | 0.290 | 330 | 4.20 |
| Diaion WA-21 | Mitsubishi Kasei Co. | polystyrene | Polyethylene polyamine | " | 5.1 | 0.325 | 560 | 4.75 |
| Sumichelate KA-800 | Sumitomo Chemical Co. | polyvinyl chloride | Polyethylene polyamine | " | 15.1 | 0.375 | 1400 | 4.12 |
| Diaion PA-418 (Comparative example) | Mitsubishi Kasei Co. | polystyrene | Quaternary ammonium salt II | —OH | 0.8 | 0.062 | 380 | 2.37 |
| Duolite | Diamond | poly- | Quaternary | " | <0.1 | <0.06 | — | 2.40 |

-continued

| Trade Name | Manufacturing company | Matrix | Feature of ion-exchange group | Functional group capable of CM-substitution | Specific surface area (m²/g-resin) | Total pore* volume (cc/g-resin) | Mean pore diameter (A) | Ion-exchange capacity (meq/g-resin) |
|---|---|---|---|---|---|---|---|---|
| A-162 (Comparative example) | Shamrock Co. | styrene | ammonium salt II | | | | | |

Note: All the numerical values were obtained by the aforesaid measurements and calculations.
*:Total volume of all the macropores having a diameter of 100 Å to 2000 Å.

The upper limits of the specific surface area and total pore volume can not strictly be determined, but too large values lower the mechanical strengths of resin. Accordingly, the specific surface area is preferably 120 m²/g-resin or less and the total pore volume is preferably 80% ore less of the resin volume.

As to the reaction solvent, using a large amount of water is not desirable, and it is desirable to confine the amount of water to 1 to 10 times by mole based on the alkaline compound and to add a water-miscible nonaqueous solvent in order to promote mixing of reagents. Such the solvent includes, for example, methanol, ethanol, acetone, dioxane, tetrahydrofuran and the like. The reaction temperature is preferably 50° C. or less in order to minimize side-reactions, and it is more preferably 5° to 30° C. in order to elevate the efficiency of the CM-reagent as much as possible. Stirring is desirably carried out to such an extent that the reagents are well mixed but the resin is not crushed.

In view of the spirit of the present invention, the ion-exchange capacity due to CM groups of the present resins need to be at least 0.5 meq/g-resin, more preferably 1.0 meq/g-resin or more. Besides, the resins need to have anion-exchange groups of at least 1 meq/g-resin. In the present invention, the ion-exchange capacity was measured batchwise as follows: For measuring anion-exchange capacity, the resin was converted to the OH-form by conditioning, and the capacity was measured by neutralization titration and expressed in a value per unit weight of the resin which was dried and weighed in the same manner as described hereinbefore. Measurement of cation-exchange capacity was same as above except that the resin was converted to the H-form by conditioning. When the CM groups are introduced into anion-exchange resins, it is natural that the apparent anion-exchange capacity per unit weight of dry resin becomes smaller than the original resins on account of weight increase due to introduced CM groups.

One of the features of the present macroporous amphoteric ion-exchange resins as an enzyme-immobilization carrier is that, so long as unreacted hydroxyl, primary amino or secondary amino groups are present in the resins, enzyme-immobilization by covalent attachment methods is also possible in addition to enzyme-immobilization by adsorption method. But, the most remarkable feature of the present resins as an immobilization carrier is that the stability (long life time) of enzymes immobilized by adsorption method is very superior as is shown in the experimental examples described hereinafter. This is very advantageous in terms of industrial use of immobilized enzymes.

Preparation of immobilized enzymes by adsorption methods is achieved by the usual ways. For example, the resins of the present invention are first activated with 0.02 M to 3 M acid or alkali solution, or bufferized with 0.02 M to 3 M buffer solution showing a buffer action in the vicinity of pH wherein an enzyme to be immobilized works well; the resins are well washed with water and well immersed in the enzyme solution so as to wet the resins far in the inner parts of macropores; and then, after stirring if necessary, the resins having immobilized enzyme thereon are filtered and washed with water. Temperature for adsorption-immobilization should be 40° C. or less, particularly preferably 10° C. or less, so long as enzymes to be immobilized are not extremely heat-resistant. The immobilized enzymes thus obtained generally contain enzyme protein of 100 mg/g-resin or more, and they are stable so long as they are not washed with salt solutions having a very high ionic strength. Enzymes immobilizable to the carriers of the present invention include not only enzymes comprising simple proteins alone but also enzymes requiring coenzymes and mixtures of one or more enzymes. Further, since the carriers of the present invention are an amphoteric ion-exchange resin, both enzymes of acidic proteins and those of basic ones may be immobilized thereto.

In the enzyme-immobilization by covalent attachment methods, on the other hand, various attachment methods making use of the reactivity of hydroxyl, primary amino, secondary amino, sulfhydryl or imido groups in the present resins may be applied. Of these methods, the following ones are particularly suitable in the respects that they are relatively simple in operation and provide stable immobilized enzymes:

(1) Attachment method with s-triazinyl derivatives such as cyanuric chloride and its derivaties
(2) Attachment method with glutaraldehyde
(3) Attachment method by an azide linkage
(4) Attachment method with monohaloacetyl derivatives In the enzyme-immobilization by covalent attachment methods, the amount of immobilized enzyme per unit weight of carrier is generally smaller than in the adsorption-immobilization. But the immobilized enzymes by this method are superior in specific activity and stability in the presence of electrolyte solution of high concentration.

The enzymes immobilizable to the carriers of the present invention are not particularly limited, and any enzyme except those which lose enzyme activity by the immobilization may be used. For example, Pronase, aminoacylase, glucose isomerase, lactase, nuclease, β-amylase, isoamylase, pullulanase, urease, deaminase, lipase, esterase, trypsin and the like may be exemplified.

The present invention will be illustrated in more detail with reference to the following examples, but the present invention is not limited to these examples within the scope of the appended claims.

EXAMPLE 1

10.0 g of Duolite A-7 was immersed in 70 ml of methanol, and a concentrated solution of 6.23 g of sodium hydroxide in 7 ml of water was added thereto. After well mixing by stirring, the mixed solution was degassed, while being cooled with ice water, for 35 minutes by an aspirator to wet the resin far in the inner part of macropores. Thereafter, a solution of 8.68 g of monochloroacetic acid in 10 ml of methanol was added, and reaction was carried out at room temperature (24°±1° C.) for 7 hours with slow stirring.

After the reaction was finished, the resin was filtered, washed with two cycles of water, 0.5 M aqueous sodium hydroxide solution, water and 0.5 M aqueous nitric acid solution, and finally washed with water sufficiently. The resin was thus converted to the H-form. Ion-exchange capacity of the introduced carboxymethyl groups was then measured.

Ion-exchange capacity: 4.82 meq/g-resin
Weight increase by CM-substitution: 3.87 g (38.7%)

It was confirmed by this weight increase that anion-exchange capacity was apparently decreased from 7.10 meq/g-resin to 5.17 meq/g-resin.

EXAMPLE 2

CM-substitution was started under the same condition as in Example 1. After 3 hours, a solution of 1.42 g of sodium hydroxide and 3.35 g of monochloroacetic acid in a mixture of 5 ml of water and 10 ml of methanol was added, and reaction was continued for further 4 hours. Cation-exchange capacity was 5.47 meq/g-resin and weight increase was 34.2%. (The reason why the ion-exchange capacity is not proportional to the weight increase in this example is not clear at present.)

EXAMPLE 3

Ten grams of Duolite A-6 was immersed in a solution of 11 g of sodium monochloroacetate in a water (10 ml)-methanol (60 ml) mixture, and the solution was degassed for 20 minutes by an aspirator while being cooled with ice water. Thereafter, a concentrated solution of 6.0 g of sodium hydroxide in 8 ml of water was added thereto, and reaction was carried out at 22°±2° C. for 6 hours with slow stirring. After the reaction was finished, the resin was filtered, washed with water and converted to the H-form by conditioning. Ion-exchange capacity of the introduced carboxymethyl groups was 3.10 meq/g-resin. Weight increase was 22.3%. Anion-exchange capacity after CM-substitution was 4.38 meq/g-resin.

EXAMPLE 4

10.0 g of Duolite S-30 which was previously well washed with an acid, alkali and water and then dried was immersed in 35 ml of an aqueous solution containing 7.2 g of sodium hydroxide. The solution was degassed for 40 minutes by an aspirator while being cooled with ice water, and then about 35 ml of water was added additionally. Thereafter, 50 ml of an aqueous solution containing 18.1 g of $\beta$-diethylaminoethyl chloride hydrochloride was added dropwise, over 2 hours with stirring, to the resin-sodium hydroxide mixed solution kept at room temperature of 22°±1° C. Reaction was continued for further 7 hours (9 hours in total). After 9 hours, the resin was filtered, washed with 0.5 M aqueous nitric acid solution, 0.5 M aqueous sodium hydroxide solution and then water, and immediately (without drying) subjected to CM-substitution as follows: All the resin obtained was immersed in a solution of 6.6 g of sodium hydroxide in a water (5 ml)-ethanol (40 ml) mixture, and the solution was slowly stirred for about 30 minutes while being cooled with ice water; and 70 ml of a methanol solution containing 13 g of sodium monochloroacetate was added and reaction was carried out at 21°±2° C. for 7 hours with slow stirring. After the reaction was finished, the resin was washed with two cycles of water, 0.5 M aqueous sodium hydroxide solution, water and 0.5 M aqueous nitric acid solution, and divided into two. The one was well washed repeatedly with water to convert to the H-form. The other was washed once more with 0.5 M aqueous sodium hydroxide solution, and then washed repeatedly with water to convert to the OH-form. Cation-exchange capacity due to the introduced carboxymethyl groups was 1.85 meq/g-resin, and anion-exchange capacity due to the introduced diethylaminoethyl groups was 1.49 meq/g-resin. In using this amphoteric ion-exchange resin as a carrier for immobilization, all the resins were converted to the H-form.

EXAMPLES 5 TO 12

Reaction coditions in which amphoteric ion-exchange resins were produced by introduction of CM groups into resins having anion-exchange groups, and properties of the resulting resins are shown in the following table. Prior to reaction, the material resins were immersed in an alkali solution or a CM-reagent solution, and the solution was degassed for 30 to 60 minutes while being cooled with ice water. For measuring cation-exchange capacity due to CM groups, the resulting resins were converted to the H-form by washing the resins in the same manner as in Example 1. For measuring anion-exchange capacity, the resulting resins were converted, after CM-substitution was finished, to the OH-form by washing.

| | | Reaction conditions | | | | | | | Results | | |
|---|---|---|---|---|---|---|---|---|---|---|---|
| Example | Material resin | Amount of material resin (g) | Amount of sodium hydroxide (g) | Amount of monochloroacetic acid (g) | Amount of water (ml) | Amount of methanol (ml) | Reaction temperature (°C.) | Reaction time (hr) | Cation-exchange capacity due to CM groups (meq/g-resin) | Anion-exchange capacity (meq/g-resin) | Remarks |
| 5 | Duolite A-4 | 9.9 | 3.3 | 8.73 | 6 | About 120 | 21 ± 2 | 7 | 2.43 | 3.78 | |
| 6 | Duolite A-4 | 5.0 | 4.0 | 8.5[1] | 3 | About 50 | 25 ± 1 | 6 | 2.15 | 3.62 | Solvent: acetone |

-continued

| Example | Material resin | Amount of material resin (g) | Amount of sodium hydroxide (g) | Amount of monochloroacetic acid (g) | Amount of water (ml) | Amount of methanol (ml) | Reaction temperature (°C.) | Reaction time (hr) | Cation-exchange capacity due to CM groups (meq/g-resin) | Anion-exchange capacity (meq/g-resin) | Remarks |
|---|---|---|---|---|---|---|---|---|---|---|---|
| 7 | Duolite A-7 | 6.0 | 1.71 | 5.26 | 2.5 | About 80 | 23 ± 2 | 6.5 | 3.56 | — | [1]Sodium monochloro acetate Solvent: Ethanol |
| 8 | Duolite S-37 | 10.0 | 7.5 | 8.5 | 10 | About 150 | 25 ± 2 | 7.0 | 2.85 | 3.57 | |
| 9 | Diaion WA-21 | 10.0 | 9.0 | 5.0 | 10 | About 100 | 22 ± 1 | 7.0 | 1.10[2] | 4.32[2] | [2]Total capacity obtained after the reaction was repeated twice under the condition mentioned left |
| 10 | Sumichelate KA-800 | 10.0 | 9.0 | 5.5 | 10 | About 100 | 20 ± 2 | 7.0 | 1.35[2] | 3.72[2] | [2]Total capacity obtained after the reaction was repeated twice under the condition mentioned left |
| 11 | Diaion WA-20 | 10.0 | 9.0 | 4.0 | 10 | About 120 | 20 ± 2 | 7.0 | 0.74[2] | 3.92[2] | |
| 12 | Amberlite IR-45 | 10.0 | 9.0 | 4.0 | 10 | About 120 | 20 ± 2 | 7.0 | 0.68[2] | — | |

Some experimental examples of immobilization of enzymes to the present carriers will be shown hereinafter.

Experiment 1

800 mg of lactase originated from *Aspergillus oryzae* [produced by Shinnihon Kagaku Kōgyō Co.; activity of the enzyme in solution, 24.1 μmoles/mg.min (pH, 4.5; 40° C; substrate, 13.3 w/v% purified lactose(] was dissolved in 40 ml of 0.02 M acetate buffer solution (pH 5.5) kept at about 4° C. 4.0 g of the CM-substituted Duolite A-7 produced in Example 1 was immersed in this solution, and the enzyme was immobilized at about 4° C. for 16 hours while shaking the solution at 80 rpm. After immobilization, the product was thoroughly washed with 0.05 M acetate buffer solution (pH 4.5) until the enzyme protein was no longer detected in the washing solution. The amount of immobilized enzyme was 149 mg/g-carrier as calculated form the amount of protein in the washing solution measured by the Lowry method. The specific activity of immobilized enzyme was 4.8 μmole/mg.min as calculated from the amount of glucose which was produced by shaking the immobilized enzyme at 80 rpm, at 40° C. and pH of 4.5, for 15 minutes with 13.3 w/v% purified lactose as a substrate.

The amount corresponding to 3.0 g of this immobilized enzyme was packed in a column equipped with a jacket of 12 mm in inside diameter, and a solution of 7 w/v% purified lactose in 0.02 M acetate buffer (pH 4.5) was passed down through the column at SV (space velocity) of 2.3 hr$^{-1}$ while maintaining the column temperature at 40° C. The decomposition rate of lactose was found to be 100% by analysis of glucose in the effluent. When a lactose solution of the same concentration was passed down for 100 days continuously under the same conditions, the decomposition rate of lactose at the 100th day was also 100%. Thus, it was found that the activity of the immobilized enzyme did not drop at all. When the same specific activity measurement as above was repeated 25 times using about 100 mg of this immobilized enzyme, the activity at 25th time was 4.7 μmoles/mg.min, which means that the activity did not drop even by the batch method.

Experiment 2

1200 mg of completely the same lactase as in Experiment 1 was dissolved in 60 ml of 0.05 M acetate buffer solution (pH 5.5). 6 g of the CM-substituted Duolite A-7 produced in Example 2 was immersed in this solution, and the enzyme was immobilized at 20±2° C. for 6 hours while stirring the solution at about 180 rpm. After immobilization, the immobilized enzyme was washed in the same manner as in Experiment 1. The amount of immobilized enzyme was 170 mg/g-resin as calculated from the amount of protein in the washing solution. The specific activity of immobilized enzyme was 5.2 μmoles/mg.min as measured under the same condition as in Experiment 1. The immobilized enzyme thus obtained was divided into two of the same amount. The one was packed in a column equipped with a jacket of 14 mm in inside diameter, and the same purified lactose solution as in Experiment 1 was passed down through the column at SV of 8.0 hr$^{-1}$. The decomposition rate of lactose by the immobilized enzyme was 95%. Decomposition of lactose was continued for 30 days through using the column in which the immobilized enzyme was packed. The decomposition rate at 30th day was 94%. Thus, it may be said that, considering a slight experimental error, the activity of immobilized enzyme did not drop at all even though used for 30 days continuously.

Experiment 3

The other half of the immobilized lactase prepared in Experiment 2 (corresponding to 3 g of the carrier) was packed in a column equipped with a jacket of 14 mm in inside diameter. A solution of 12 w/v% purified lactose in the same buffer solution as in Experiment 1 was passed down through the column at SV of 5.0 hr$^{-1}$ for 30 days continuously. The decomposition rate of lactose calculated from the amount of glucose in the effluent was 91±2.5% over 30 days, which means that the activity of immobilized enzyme did not drop at all.

Experiment 4

600 mg of lactase originated from *Aspergillus oryzae* [produced by Shinnihon Kagaku Kōgyō Co.; activity of the enzyme in solution, 50.9 μmoles/mg.min (pH, 4.5; 40° C; substrate, 13.3 w/v% purified lactose)] was dissolved in 30 ml of 0.05 M acetate buffer solution (pH 5.5). 3.0 g of the CM-substituted Duolite A-4 produced in Example 5 was immersed in this solution, and the enzyme was immobilized at about 20° C. for 7 hours while stirring the solution at 180 rpm. After immobilization, the immobilized enzyme was washed in the same manner as in Experiment 1. The amount of immobilized enzyme was 118 mg/g-carrier. The specific activity of immobilized inzyme was 9.2 μmoles/mg.min as measured under the same condition as in Experiment 1. This immobilized enzyme was packed in a column equipped with a jacket of about 13 mm in inside diameter, and the same purified lactose solution as in Exmperiment 1 was passed down through the column at 40° C. and at SV of 5.0 hr$^{-1}$ for 30 days continuously. The decomposition rate of lactose was kept 100% over 30 days, and loss in enzyme activity was not observed. Continuous decomposition of lactose was continued for further 20 days in the same manner as above except that SV was increased to 8.0 hr$^{-1}$. Decomposition rate was still kept at 100%. Thus, it was found that the activity did not drop at all even though the immobilized enzyme was used for 50 days continuously.

Experiment 5

100 mg of a commercially available papain was dissolved in 30 ml of 0.02 M phosphat buffer solution (pH 6.2) kept at 4° C. 1.0 g of the CM-substituted Duolite A-4 produced in Example 6 was immersed in this solution, and the enzyme was immobilized at 4° to 10° C. for 10 hours while stirring the solution at about 150 rpm. The immobilized enzyme was washed thoroughly with 0.05 M phosphat buffer solution (pH 6.2), 0.1 M aqueous sodium chloride solution and ion exchange water in this order. The washing solution was recovered and measured for the amount of protein by the Lowry method. By calculation from the said amount, the amount of immobilized enzyme was found to be 76 mg/g-carrier. The specific activity of immobilized enzyme was measured at 40° C. and pH 6.2 by means of a pH-stat (Hiranuma pH-stat sp-11) using 0.28 M N-benzoyl-L-arginine ethyl ester (BAEE) as a substrate, and it was found to be 2.7 μmoles/mg.min. This value corresponds to 35% of the specific activity of original enzyme in solution. Measurement of the specific activity of this immobilized papain was repeated 15 times in the same manner as above, and the activity at the 15th time was 98% of that at the first time, which means that there was little loss in activity. The above measurements of the activities of the immobilized enzyme and the enzyme in solution was carried out in the presence of $2\times10^{-3}$ M ethylenediamine tetraacetic acid, $5\times10^{-3}$ M cysteins and 0.1 M sodium chloride.

Experiment 6

60 mg of a commercially available purified trypsin was dissolved in 15 ml of 0.05 M Tris-HCl buffer solution (pH 7.5) kept at about 4° C. 1.0 g of the CM-substituted Duolite S-37 produced in Example 8 was added to this solution, and the enzyme was immobilized at about 4° C. while slowly stirring the solution at about 60 rpm. After 10 hours, the immobilized trypsin was filtered and well washed with 0.05 M Tris-CHl buffer solution, 0.1 M sodium chloride solution and distilled water in this order. The washing solution was recovered and measured for the amount of protein by ultraviolet absorption intensity. By calculation from the said amount, the amount of immobilized enzyme was found to be 56 mg/g-carrier. The specific activity of immobilized trypsin was measured by means of a pH-stat at 30° C. and pH 7.5 in the presence of 0.02 M calcium chloride using BAEE as a substrate, and it was found to be 5.8 μmoles/mg.min. This value corresponds to 22% of the specific activity of original enzyme in solution. Using about 100 mg of this immobilized trypsin, measurement of specific activity was repeated 5 times under the same condition as above with BAEE as a substrate. As a result, the specific activity at the 5th time was 4.6 μmoles/mg.min.

Experiment 7

20 ml of 0.1 M phosphate buffer solution (pH 6.7) containing 1250 Sumner unit of a commercially available urease (purchased from Tōkyō Kasei Co.) was prepared. 1.0 g of the CM-substituted Diaion WA-21 produced in Example 9 was added to the solution, and stirred at about 60 rpm at about 4° C. for 16 hours. After immobilization, the immobilized enzyme was filtered and thoroughly washed with 0.05 M phosphate buffer solution and then distilled water until protein was no longer detected in the filtrate. The amount of immobilized enzyme was calculated as 382 Sumner unit/g-carrier. The activity of immobilized enzyme was measured from a time required for 0.1 M phosphate buffer solution containing 3.0% by weight of urea to change its pH from 6.7 to 7.7 at 20° C., and it was found to be 412 Sumner unit/g-carrier.

Note (1): One Sumner unit refers to the amount of enzyme which decomposes urea corresponding to 1 mg of ammonia nitrogen at 20° C. and pH 7.0 during 5 minutes in a phsphate buffer solution.

Experiment 8

Glucose isomerase extracted from *Streptomyces* sp. (produced by Nagase Sangyō Co.) and purified which has activity of 36,000 unit and 255 mg of protein (measured by the Lowry method), was dissolved in 30 ml of 0.05 M phosphate buffer solution (pH 7.65). 3.0 g of the CM-substituted Duolite A-7 produced in Example 1 was added to the solution, and immobilization was carried out at room temperature (about 18° C.) for 9 hours while stirring the solution at about 120 rpm. After immobilization, the immobilized enzyme was filtered and well washed with 0.1 M phosphate buffer solution (pH 7.65). By measurements of the activity of the filtrate and the amount of protein in the filtrate, it was found that the activity of immobilized protein was 9500 unit/g-carrier and the amount of immobilized protein was 61 mg/g-carrier. The immobilized glucose isomerase thus obtained was filled in a column equipped with a jacket of 12 mm in inside diameter, and 54 w/v% aqueous purified glucose solution (pH 7.65, containing $5 \times 10^{-3}$ M $MgSO_4.7H_2O$) was passed down through the column at SV of 2.0 $hr^{-1}$ while maintaining the column temperature at 60° C., whereby isomerization of glucose was carried out. Conversion was kept at 50 to 51% for about 500 hours after beginning of the isomerization, and then it gradually decreased.

Note (2): One unit of glucose isomerase refers to the amount of enzyme which produces 1 mg of fructose when reaction is carried out at 70° C. and pH 7.0 for 1 hour, with 0.1 M D-glucose solution as a substrate, in 0.05 M phosphate buffer solution containing 0.005 M $MgSO_4.7H_2O$.

Note (3): Measurement of fractose was carried out by the cysteine-carbazole-sulfuric acid method according to JAS.

Experiment 9

200 mg of pullulanase originated from *Aerobacter aerogenes* (produced by Nagase Sangyō Co.) was dissolved in 30 ml of 0.02M acetate buffer solution (pH 5.0). 3 g of the CM-substituted Diaion WA-21 produced in Example 9 was added to the solution, and the enzyme was immobilized at about 10° C. for 16 hours with slow stirring. The amount of the immobilized enzyme was calculated from the recovered washing solution and it was 43 mg/g-carrier. All of the immobilized enzyme was packed in a column equipped with a jacket of 12 mm in inside diameter, and a 1.0% purified pullulane solution (pH 5.0) was passed down through the column at SV of 1 $hr^{-1}$ for 10 days continuously while maintaining the column temperature at 40° C. The amount of maltotriose in the effluent was measured by the Somogyi-Nelson method, and it was found that conversion to maltotriose was kept unchanged at 95±4% for 10 days.

Experiment 10

Using 600 mg of the same lactase as used in Experiment 1, the lactase was immobilized to 3.0 g of a carrier, the CM-substituted Diaion WA-20 produced in Example 11, under the same condition as in Experiment 1. The amount of immobilized enzyme was 98 mg/g-carrier as calculated from the amount of protein in the washing solution. The specific activity of immobilized enzyme was 4.5 $\mu$moles/mg.min as measured under the same conditions as in Experiment 1. Using about 100 mg of this immobilized lactase, the specific activity measurement was repeated 15 times using a new lactose solution at every measurement, and the activity at the 15th time was 3.5 $\mu$moles/mg.min. It is known from the results that the carrier produced in Example 11 was a little inferior to that produced in Example 1 in operational stability of immobilized enzyme. One of the reasons may be considered due to that the amount of introduced CM groups in Example 11 is smaller. It is however, clear that the immobilized enzyme produced in Example 11 is more stable (i.e. longer in life time) than that produced in the following reference example.

Reference Experiment

The experiment was carried out in the same manner as in Experiment 10, except that a weakly basic macroporous ion-exchange resin, Diaion WA-20, was used as a carrier taking into account that lactase originated from *Aspergillus oryzae* is an acidic protein. The amount of immobilized enzyme was 79 mg/g-carrier and the specific activity of immobilized enzyme was 3.6 $\mu$moles/mg.min. This specific activity measurement was repeated 10 times, but the activity dropped to 1.4 $\mu$moles/mg.min at the 5th measurement and to 0.3 $\mu$moles/mg.min at the 10th measurement. As is clear from the above results, stable immobilized enzymes withstanding industrial use could not be obtained.

Experiment 11

2.0 g of the CM-substituted Duolite A-4 produced in Example 6 was immersed in 20 ml of 1 N sodium hydroxide solution. The solution was degassed at 4° C. for 15 minutes and the excessive alkali solution was removed by filtration. This resin was immersed in 25 ml of dioxane at room temperature (about 20° C.) for 5 minutes with stirring, and then 20 ml of a previously prepared dioxan solution containing 4 g of cyanuric chloride was added thereto, followed by vigorous stirring at room temperature. After 3 minutes, 25 ml of cold water was added to the reaction solution and, after 5 seconds, 25 ml of acetic acid was added to stop the reaction. The mixed solution was filtered, and the resin was immediately washed with cold water and cold acetone. The resin was then added to 30 ml of 0.05 M phosphate buffer solution (pH 7.8) containing 220 mg of a commercially available enzyme, Pronase E, originated from *Streptomyces griseus*. The solution was stirred at about 4° C. and kept at pH 7.8 with addition of 0.2 N sodium hydroxide solution. Immobilization was then carried out for 5 hours. The immobilized enzyme was filtered and thoroughly washed with ice-cooled 1 M sodium chloride solution, 0.1 M phosphate buffer solution and ice-cooled water in this order until protein was no longer detected in the washing solution. The amount of immobilized enzyme was 86 mg/g-carrier. The specific activity of immobilized enzyme was measured by means of a pH-stat at 40° C. and pH 6.0 with a 20% DL-lysine methyl ester as a substrate, and it was found to be 2.7 $\mu$moles/mg.min.

Next, using about 100 mg of this immobilized enzyme, experiment was repeated batchwise at 40° C. and pH 6.0 with 10 ml of 10% L-lysine methyl ester as a substrate. Required time per experiment was fixed to 40 minutes and reaction rate was measured by a pH-stat. In this way, the number of experiments which were repeated until reaction rate dropped to half of the first reaction rate was obtained. The number thus obtained was called "half life number". The half life number of this immobilized enzyme was 83.

Experiment 12

Two grams of the CM-substituted Duolite A-7 produced in Example 2 was immersed in methanol, converted to methyl ester with hydrogen chloride gas, thereafter to hydrazide with hydrazine hydrate and finally to azide with 3% sodium nitrite solution. Immediately, the product was immersed in 20 ml of a phosphate buffer solution containing 1000 Sumner units of a commercially available urease (purchased from Tōkyō Kasei Co.). Thereafter, the enzyme was immobilized at about 4° C. for 16 hours with mild shaking. The immobilized enzyme was washed with 5 N sodium chloride solution, 0.1 M phosphate buffer solution (pH 6.7) and ion-exchange water in this order. The activity of immobilized enzyme was measured by colorimetry at 20° C. using a 3.0% urea solution as a substrate, and it was found to be 290 Sumner unit/g-carrier. Using this immobilized urease, the experiment was repeated 10 times but loss in activity was hardly observed.

Experiment 13

2.0 g of the Amphoteric-ionized Duolite S-30 produced in Example 4 was immersed in 20 ml of a dioxane solution containing 25 g of bromoacetic acid, followed by slow stirring at room temperature for 8 hours. Thereafter, 17 ml of bromoacetyl bromide was gradually added dropwise, followed by stirring for about 6 hours. After the reaction was finished, bromoacetylated resin was obtained by washing with ice-cooled 0.1 M sodium carbonate solution and then ice-cooled water. This resin was immersed in 0.2 M phosphate buffer solution (pH 8.5) containing 100 mg of aminoacylase (produced by Amano Seiyaku Co., 15,000 unit/g), and the enzyme was immobilized at about 4° C. for 18 hours with slow stirring. The resulting immobilized enzyme was washed repeatedly. The activity of this immobilized enzyme was measured at 37° C. with 0.2 M N-acetyl-DL-methionine solution (pH 7.0, containing $1 \times 10^{-4}$ mole of $CoCl_2$) as a substrate, and it was found that the activity was 270 unit/g-carrier from the amount of produced L-methionine. All the immobilized enzyme thus obtained was packed in a column equipped with a jacket of 10 mm in inside diameter, and the same N-acetyl-DL-methionine solution as used in the activity measurement was continuously passed down through the column at SV of 1.1 $hr^{-1}$ while maintaining the column temperature at 40° C. The hydrolysis rate of the L-isomer after one day was 99% and loss in enzyme activity was hardly observed even after 10 days.

What is claimed is:

1. An enzyme-immobilization carrier which comprises a macroporous, synthetic amphoteric ion-exchange resin having a specific surface area of at least 1 m²/g-resin containing macropores with a pore diameter of 100 Å to 2,000 Å, of which total volume is at least 0.1 cc/g-resin; said resin comprising (a) a phenol resin matrix having a primary amino group, secondary amino group, tertiary amino group, quaternary ammonium group or a mixture thereof as an anion-exchanger and a carboxymethyl group linked to the matrix through a phenolic ether linkage or to said primary or secondary amino group, wherein the cation=exchange capacity due to the carboxymethyl group is not less than 0.5 meq/g-resin and the anion-exchange capacity due to the amino group, substituted amino groups or the mixture thereof is not less than 1 meq/g-resin, or (b) a polystyrene or polyvinyl chloride matrix having at least a primary amino group, secondary amino group or a mixture thereof as an anion-exchanger and a carboxymethyl group linked to said primary or secondary amino group, wherein the cation-exchange capacity due to the carboxymethyl group is not less than 0.5 meq/g-resin and the anion-exchange capacity due to the amino group, substituted amino groups or the mixture thereof is not less than 1 meq/g-resin.

2. An enzyme-immobilization carrier according to claim 1, wherein said cation-exchange capacity is not less than 1 meq/g-resin.

3. An enzyme-immobilization carrier according to claim 1, wherein said specific surface area of the macroporous synthetic amphoteric ion-exchange resin is not less than 5 m²/g resin.

4. An enzyme-immobilization carrier according to claim 1, wherein the mean pore diameter of the pores in said resin is in the range of 150 Å to 1000 Å.

5. An enzyme-immobilization carrier according to claim 1, wherein said total volume of macropores with a pore diameter of 100 Å to 2000 Å is at least 0.2 cc/g-dry resin.

6. A process for producing an enzyme-immobilization carrier comprising a macroporous, synthetic amphoteric ion-exchange resin having a carboxymethyl group of which the cation-exchange capacity is not less than 0.5 meq/g-resin and an amino group, a substituted amino group or a mixture thereof which the anion-exchange capacities are not less than 1 meq/g-resin, which comprises reacting a compound of the formula:

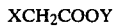

wherein X is halogen and Y is hydrogen or an alkali metal with (a) granules or beads of a solid, macroporous phenol resin having a primary amino group, a secondary amino group or a mixture thereof, or (b) beads of a macroporous polystyrene or polyvinyl chloride resin having a primary amino group, secondary amino group or a mixture thereof, having a specific surface area of at least 1 m²g-resin and containing macropores of which the total volume of those with a pore diameter from 100 Å to 2,000 Å is at least 0.1 cc/g-resin in the presence of an alkaline compound.

7. A process according to claim 6, wherein said cation-exchange capacity is not less than 1 meq/g-resin.

8. A process according to claim 7, wherein the alkaline compound is sodium hydroxide.

9. A process according to claim 6, wherein said specific surface area of the macroporous, synthetic amphoteric ion-exchange resin is not less than 5 m²g resin.

10. A process according to claim 6, wherein the mean pore diameter of the pores in said resin is in the range of 150 Å to 1000 Å.

11. A process according to claim 6, wherein said total volume of macropores with a diameter of 100 Å to 2000 Å is at least 0.2 cc/g-dry resin.

12. A process according to claim 6, wherein said compound is chloroacetic acid or sodium chloroacetate.

* * * * *